United States Patent [19]

Kydonieus et al.

[11] Patent Number: 5,580,573

[45] Date of Patent: Dec. 3, 1996

[54] TEMPERATURE ACTIVATED CONTROLLED RELEASE

[75] Inventors: Agis Kydonieus, Kendall Park; Kishore R. Shah, Bridgewater, both of N.J.; Stefanie C. Decker, Staten Island, N.Y.

[73] Assignee: E. R. Squibb and Sons, Inc., Princeton, N.J.

[21] Appl. No.: 88,496

[22] Filed: Jul. 7, 1993

Related U.S. Application Data

[63] Continuation of Ser. No. 951,023, Sep. 24, 1992, abandoned, which is a continuation-in-part of Ser. No. 649,381, Feb. 1, 1991, abandoned.

[51] Int. Cl.$^6$ ............................................. A61F 13/02
[52] U.S. Cl. ..................... 424/449; 424/448; 424/486; 424/487
[58] Field of Search ................................. 424/448, 449, 424/486, 487

[56] References Cited

U.S. PATENT DOCUMENTS

| | | | |
|---|---|---|---|
| 4,661,104 | 4/1987 | Von Bitteva et al. | 604/896 |
| 4,830,855 | 5/1989 | Stewart | 424/449 |
| 4,840,796 | 6/1989 | Sweet et al. | 424/448 |
| 4,874,119 | 11/1989 | Konner et al. | 424/449 |
| 4,908,208 | 3/1990 | Lee et al. | 424/409 |
| 4,951,657 | 8/1990 | Pfister et al. | 128/156 |

FOREIGN PATENT DOCUMENTS

| | | |
|---|---|---|
| 338820 | 10/1989 | European Pat. Off. . |
| 338732 | 10/1989 | European Pat. Off. . |

*Primary Examiner*—Jyothsna Venkat
*Attorney, Agent, or Firm*—Theodore R. Furman, Jr.; John M. Kilcoyne

[57] ABSTRACT

A polymeric device for the controlled release of active agents contained in the device in which the polymer has a glass transition temperature greater than the normal storage or non use temperature of the device. When heated to or above the glass transition temperature of the polymer, the active agent is released. The release of active agent can be switched on or off by the adjustment of the temperature of the polymeric device above or below the glass transition temperature of the polymer.

8 Claims, 2 Drawing Sheets

TEMPERATURE ACTIVATED CONTROLLED RELEASE

This is a continuation of application Ser. No. 951,023 filed Sep. 24, 1992 abandoned; which is a continuation-in-part of Ser. No. 649,381 filed Feb. 1, 1991, now abandoned.

BACKGROUND OF THE INVENTION

1. Field of the Invention

This invention relates to a device for the controlled release of biologically active substances and other chemical materials. More particularly, this invention relates to a controlled delivery system for biologically active substances and other chemical materials. Still more particularly, this invention relates to a polymeric system for controlled release in which the release of materials is capable of being switched on or off by adjustment of temperature above or below the glass transition temperature of the polymeric material.

2. Description of the Prior Art

R. F. Stewart (U.S. Pat. No. 4,830,355) has utilized the phenomenon of crystalline melting transition (Tm) in a side chain crystallizable polymer to accomplish the temperature activated controlled released of active agents. At temperatures below the melt temperature of the polymer, the polymer is effectively non-permeable and it acts as a membrane barrier with extremely low diffusional rates for most active agents. In this non-permeable state, the polymer has the ability to protect and contain the desired agent. Above the Tm, the polymer is highly permeable with correspondingly high diffusional rates. The temperature activated release occurs when the polymeric device is heated above its Tm.

T. Okano and coworkers [J. of Contr. Rel. 11, p. 255 (1990)] have described on-off switching polymers for drug permeation and release controlled by temperature change. In this system, water swollen cross-linked interpenetrating network of poly(N-isopropylacrylamide) and polyurethane is used as the drug matrix. A decrease in temperature of the gel results in higher drug release rates due to "gel squeezing effect".

R. P. Sweet, et al. (U.S. Pat. No. 4,840,796) describe a copolymer drug delivery system having soft and hard segments. The soft segment is polydiorganosiloxane having a low Tg of about −125° C. while the hard segment has a high Tg. The copolymer matrix is therefore drug permeable at all practical temperatures, i.e, above −125° C.

SUMMARY OF THE INVENTION

One of the important properties affecting the diffusivity of a solute through a polymeric material is the glass transition temperature (Tg) of the material. The glass transition of a polymer is the temperature region within which the amorphous (noncrystalline) chain segments change from a soft material to a hard brittle solid. A polymer exists in a rubbery state above its Tg. The glass transition region signifies the onset of coordinated motion in a polymer chain. At low temperature, only vibrational motions are possible, and the polymer is hard and glassy. Above the Tg, the chain segments attain sufficient thermal energy to move in a coordinated manner. We have unexpectedly found that when the chain segments move in a coordinated fashion the diffusion through the polymer is magnitudes higher, e.g. 100 fold increase. We have also unexpectedly found that below the Tg when there is no coordinated chain segment motion, the diffusion is zero or undetectable. The present invention pertains to the devices for controlled release of biologically active substances in which the release is temperature activated. More specifically, the active agent release occurs upon raising the temperature of the polymeric device just above its Tg.

The polymeric material for the device construction is selected such that its Tg is in the temperature range at which the active agent release is desired. The ambient or normal storage temperatures for the device are below its Tg, under which conditions insignificant release of the active agent occurs due to its very low diffusivity through the polymeric matrix. Upon heating the device above its Tg, greatly increased release of the active agent occurs because of the sudden corresponding increase in diffusivity of the agent through the polymeric matrix. Thus, "on demand" release of the active agent can be affected by means of temperature activation utilizing the phenomenon of glass transition in polymers.

DESCRIPTION OF THE INVENTION

An object of the present invention is to provide a polymeric device for controlled release of biologically active agents, such that the glass transition temperature (Tg) of the polymer is greater than the normal storage temperatures for the device. The polymeric device controlling the release of the active agent has its Tg at the selected environmental use temperature. The release rates of the active agent from the device under the storage conditions are very low and negligible. When the device is placed in the desired use environment, sudden release of the active agent occurs at rates which are considerably greater than those under the storage conditions. The effective release rate under the use conditions is governed by solubility and concentration of the active agent in the polymer, and by the device construction. Polymers having a Tg within the range of about 20° to 50° C. are preferred and those having a Tg in the range 25° to 45° C. are most suitable for drug delivery.

Figure 1:
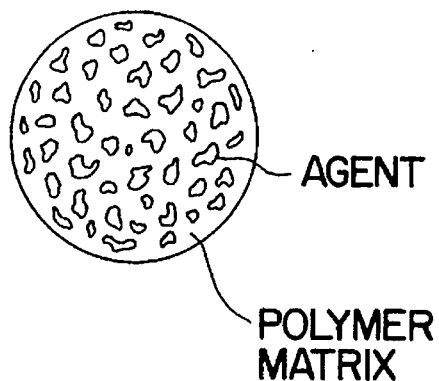
FIG. 1 is a cross-sectional view of one embodiment of the device of this invention in which the active agent is dispersed throughout a matrix of rate controlling polymer.
Figure 2:
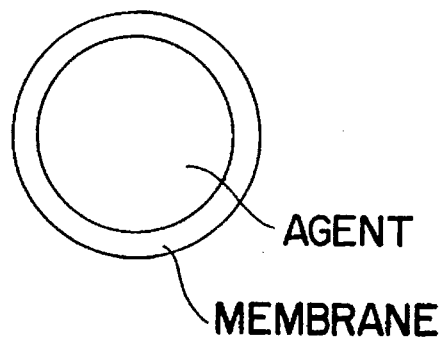
FIG. 2 is a cross-sectional view of another device of this invention in which the active agent is encapsulated by the rate controlling polymer.
Figure 3:
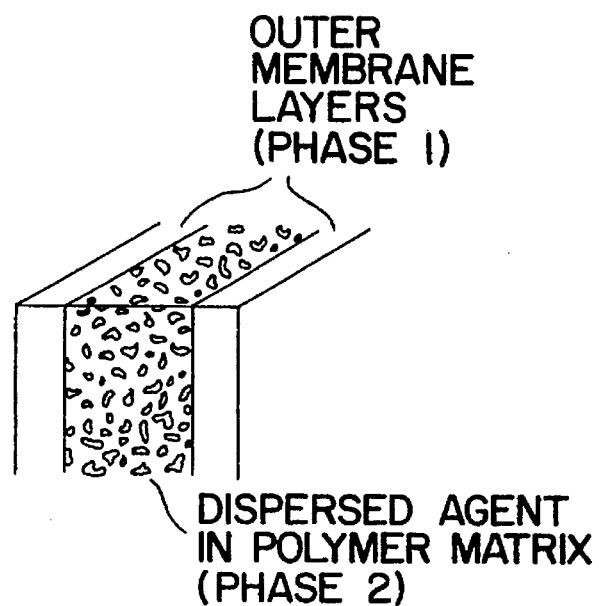
FIG. 3 is a cross-sectional view of another device of this invention in which the active agent is dispersed in polymer and the active agent containing polymer matrix is encapsulated by the rate controlling polymer.

The construction of the polymeric devices of this invention can be classified as either monolithic (matrix) (FIG. 1), reservoir (FIG. 2) or combined monolithic-reservoir (FIG. 3). In the monolithic system, the active agent is uniformly dispersed and/or dissolved in the release rate controlling polymer. In the reservoir system, the rate controlling polymer forms the walls or the membrane of a capsule in which the active agent is contained. Whereas, in the combined monolithic-reservoir system, the active agent is dispersed and/or dissolved in polymer which has its Tg significantly below the use temperature. This active agent containing polymer matrix is encapsulated by the rate controlling polymer. In all of these device constructions, the rate controlling polymer has its Tg as specified above, its exact value being dependent upon the environmental use temperature for the desired application. The precise shape (slab, sphere, or other) of the device is also governed by requirements of the given application.

The devices of the present invention are suitable for "on-demand" controlled release of active agents which include biologically active agents such as therapeutic drugs, antimicrobials, contraceptive agents, pesticides, fungicides, flavors, fragrances, or the like. These devices particularly lend themselves to transdermal drug delivery and for topical application of dermatologically acting agents. In addition, these devices are useful for controlled delivery of medications to the wounds. Another potential application can be subdermally implantable devices which can be activated by externally applied thermal energy. They can also be used internally. Other examples of biologically active agents that may be suited for use in this invention are found in the U.S. Pat. No. 4,830,355. The present invention may also be suitably utilized for the controlled release of non-bioactive chemicals or other substances in nonbiologic and/or industrial application. Such a use is controlled release of a catalytic agent in a chemical reaction mixture.

The release rate controlling polymeric composition can be selected from most of the commercially available polymeric materials such as poly(vinyl acetate), polystyrene, poly(alkyl acrylates), poly(alkyl methacrylates), modified cellulosics, poly(vinyl pyrrolidone), aliphatic polyesters, and vinyl chloride polymers and their copolymers. The Tg of some of the known polymers are shown in Table I. Additional polymeric materials with their Tg which can be used are described in *Polymer Handbook*, Third Edition 1989, J. Wiley & Son, J. Brandrup and E. H. Immergut beginning at Page 213. Copolymerization of an alkyl acrylate or an alkyl methacrylate with other members of the acrylate and methacrylate homologous series and/or with other copolymerizable ethylenically unsaturated monomers is a particularly convenient method of preparing materials having the desired Tg. Such copolymers can be prepared by conventional solution, emulsion, or suspension polymerization initiated by free radicals. In addition, the Tg of any and all of these polymeric materials can be altered to the desired range by appropriate plasticization. In addition, copolymers can be formed which are not completely compatible. In this case, two separate Tg's exist and therefore two temperatures for "on-demand" increase in diffusion but both being above the storage or non-use temperature.

The non-rate controlling polymer, containing the active agent for use in the combined monolithic-reservoir type device constructions, is usually a polymer having a low Tg. Examples of such polymers include, but are not limited to, $C_2$–$C_8$ alkyl acrylate polymers and their copolymers, poly(vinyl alkyl ethers), polyisobutylene, and polysiloxanes.

In order to ensure the necessary dimensional stability of the device, molecular weights of its polymeric components are usually very high.

The solution or dispersion of the active agent in either the rate controlling or the non-rate controlling polymer, as may be the case, can be prepared by dissolving the agent together with the polymeric component in a suitable solvent and then removing the solvent by evaporation. Such a mixture may also be prepared in a conventional process equipment like a banbury or a sigma-blade mixer under the influence of heat.

The device may be fabricated by employing conventional plastics fabrication methods.

The following examples are intended to illustrate the invention described herein without unduly restricting it.

EXAMPLES

1. Permeation of salicylic acid through three different polymeric membranes [poly(n-propyl methacrylate), poly(isobutyl methacrylate), and poly(ethyl methacrylate)] at different temperatures was studied, as described below, employing Franz-type diffusion cells.

A) Materials: Poly(n-propyl methacrylate), poly(isobutyl methacrylate) and poly(ethyl methacrylate) were obtained from Scientific Polymer Products, Inc. Salicylic acid for Fisher Scientific was used as the permeant.

B) Methods:

DSC Analysis: The Tg of each polymer was measured using a Perkin Elmer DSC-4 Differential Scanning Calorimeter. Samples of polymer were taken directly from the bottle and placed in a sample dish. The scan ranged from 20°–120° C. and increased at a rate of 10 deg/min. The Tg was determined graphically using the TADS data analysis program.

Diffusion Experiments: Films for diffusion experiments were prepared by dissolving each polymer in toluene at 30% solids and then casting the solutions on release liner to give 2.5 mil films.

Diffusion experiments were done using Franz diffusion cells. Three cells per polymer were placed in aluminum blocks in Pierce Reacti-Therm Heating/Stirring Modules which were used to control the temperature. Temperatures were monitored with thermometers set in the aluminum block and insulation material was wrapped around each set of cells.

Figure 4:
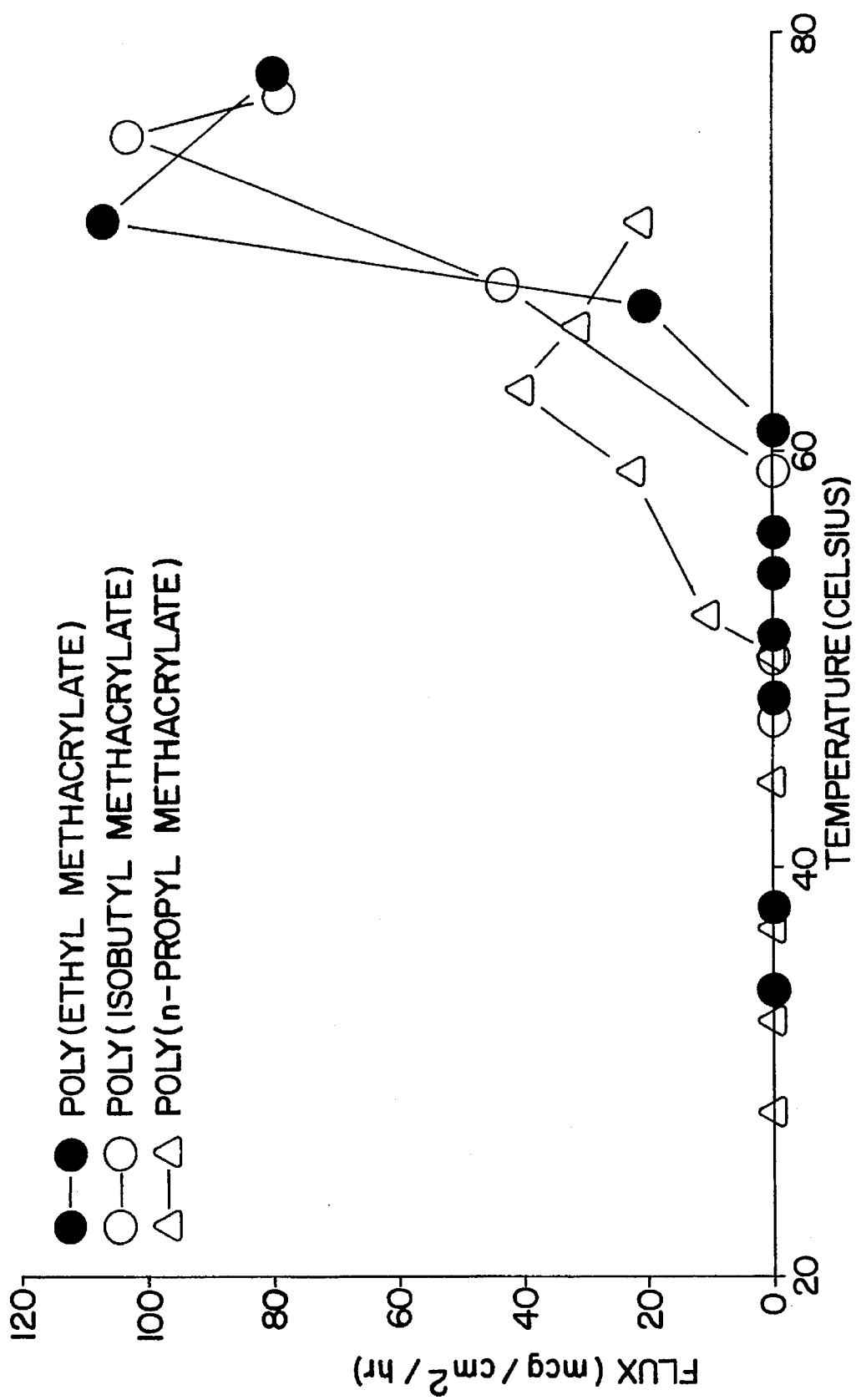
FIG. 4 is a graph showing the effect of membrane upon the salicylic acid flux for several rate controlling polymers used in the devices of this invention.

Approximately one cc of saturated aqueous salicylic acid solution was placed in the donor compartments of the difusion cells. The receptor compartment held 7.5 cc of deionized water. The experiments lasted approximately four days during which time the cells were sampled, complete removal and replacement of receptor solution, several times a day each time raising the block temperature. The samples were analyzed with a Perkin Elmer Lambda 3B UV/VIS Spectrophotometer at wavelength 296 nm. The release kinetics were studied for the salicylic acid permeation through each of the membranes at different temperatures. In each case, the system exhibited zero-order kinetics. The permeation rate at each temperature was calculated from the slope of a plot of the cumulative amount permeated versus time. FIG. 4 shows the effect of membrane temperature upon the salicylic acid flux for poly(ethyl methacrylate), poly(n-propyl methacrylate), and poly(isobutyl methacrylate), respectively. The maximum in the salicylic acid flux corresponded very closely to the observed Tg of the individual polymeric membranes (Table II) and the onset temperatures for the glass transition corresponded with the permeation starting temperatures.

2. Monolithic controlled release devices were also prepared and tested. Thirty grams of poly(n-propyl methacrylate) and 0.3 grams of timolol base were dissolved in 100 grams of ethyl acetate.

The solution was cast on release liner and the solvent evaporated. The resulting film was 2.5 mils thick containing 1 percent timolol.

Diffusion experiments were performed using Franz diffusion cells as described above. The film was placed between the donor and receptor compartments of the diffusion cell with the receptor compartment filled with 7.5 cc of a pH 4.0 phosphate buffer solution. The donor compartment was left empty. At temperatures below 50° C. no timolol was detected in the receptor phase. At the temperature of 70° C. the release rate of timolol was 4 mg/cm$^2$/hr.

TABLE I

GLASS TRANSITION TEMPERATURES OF SOME COMMON POLYMERIC MATERIALS

| POLYMER | Tg, °C. |
| --- | --- |
| Poly(vinyl acetate) | 31 |
| Poly(styrene) | 100 |
| Poly(methyl methacrylate) | 105 |
| Poly(methyl acrylate) | 10 |
| Poly(n-butyl acrylate) | −54 |
| Poly(n-butyl methacrylate) | 20 |
| Poly(vinyl chloride) | 98 |
| Poly(phenyl acrylate) | 57 |
| Poly(cyclohexyl methacrylate) | 83 |
| Poly(3,3-dimethylbutyl methacrylate) | 45 |

TABLE II

EFFECT OF POLYMER GLASS TRANSITION UPON STARTING AND MAX. RATE TEMPERATURES FOR SALICYLIC ACID PERMEATION

| | Temperature, °C. | | | |
| --- | --- | --- | --- | --- |
| Membrane | Glass Transition onset Temperature | Permeation Start | Tg Obs.(DSC) | Permeation Max |
| Poly(ethyl methacrylate) | 66 | 62 | 76 | 71 |
| Poly(n-propyl methacrylate) | 52 | 50 | 64 | 63 |
| Poly(isobutyl methacrylate) | 62 | 59 | 75 | 73 |

While this invention has been described and exemplified in terms of its preferred embodiment, those skilled in the art will appreciate that modifications can be made without departing from the spirit of the invention.

We claim:

1. A method of controlling the release of an active agent from a polymeric device which does not release any significant amount of the active agent under storage conditions, wherein the polymeric device consists essentially of an amorphous polymer and an active agent contained therein, said amorphous polymer having a glass transition temperature greater than the storage temperature of said device and about the temperature at which the release of the active agent is desired, wherein at temperatures below the glass transition temperature no substantial release of active agent occurs through the amorphous polymer and at a temperature at or above the glass transition temperature of said amorphous polymer an effective amount of active agent is released, which comprises heating the polymeric device to at least the glass transition temperature of the amorphous polymer of said device, wherein the glass transition temperature is from about 25° to about 50° C.

2. The method of claim 1 wherein the device comprises a reservoir containing the active agent and a polymeric membrane surrounding the reservoir wherein the glass transition temperature of said membrane is substantially equal to the temperature desired for the device to initiate release of the active agent.

3. The method of claim 1 wherein the device comprises a polymer within which the active agent is dissolved or dispersed wherein the glass transition temperature of said polymer is substantially equal to the temperature desired for the device to initiate release of the active agent.

4. The method of claim 1 wherein the active agent is released transdermally.

5. The method of claim 1 wherein the active agent is released subdermally.

6. The method of claim 1 wherein the active agent is released into a wound.

7. The method of claim 1 wherein the active agent to be released is a biologically active agent.

8. The method of claim 1 wherein the active agent is a drug, pesticide, fungicide or fragrance.

* * * * *